United States Patent [19]
Loffet et al.

[11] Patent Number: 5,498,732
[45] Date of Patent: Mar. 12, 1996

[54] PROCESS FOR THE STEREOSPECIFIC PREPARATION OF 5-(1-HYDROXY-2-URETHANETHYLIDENE)-2,-DIMETHYL-1,3-DIOXANE-4,6-DIONE DERIVATIVES, WHICH ARE PRECURSORS OF CHIRAL TETRAMIC ACID DERIVATIVES

[75] Inventors: Albert Loffet, Paris; Jean-Alain Fehrentz, Saint Nazaire de Pezan; Jean Martinez, Saussan; Philippe-François Winternitz, Montpellier, all of France

[73] Assignee: Propeptide, Vert le Petit, France

[21] Appl. No.: 305,305

[22] Filed: Sep. 15, 1994

[30] Foreign Application Priority Data

Sep. 15, 1993 [FR] France .................. 93 10965

[51] Int. Cl.[6] ............................................. C07D 319/06
[52] U.S. Cl. ............................................. 549/274
[58] Field of Search ............................................. 549/274

[56] References Cited

PUBLICATIONS

Jiang et al, "Comparative Study of Selected Reagents for Carboxyl Activation", Tetrahedron Letters, vol. 34, No. 42, Aug. 1993, pp. 6705–6708.
Wuts et al., Synthesis, 1989, 951.
Poncet, et al., J. Chem. Soc. Perkin, Trans. 1, 1990, 611.
Fuller, et al., J. Chem. Soc. vol. 112, No. 20, 1990, 7414–7416.
J. Maibaum, et al., Synthesis of The Novel Py—(Bezylozymethyl)—Protected Histidine Analogue of Statine, Journal Journal of Medicinal Chemistry, vol. 32, No. 7, 1989 1571–1576.
P. Jouin, et al., Stereospecific Synthesis of N–protected Statine and Its Analogues Via Chiral Tetramic Acid, Journal of The Chemical Society, Perkin Trnsactions 1, No. 1, 1987, 1177–1182.

*Primary Examiner*—Nicky Chan
*Attorney, Agent, or Firm*—Cushman Darby & Cushman

[57] ABSTRACT

The invention relates to a process for the preparation of 5-(1-hydroxy-2-urethanethylidene)-2,2-dimethyl-1,3-dioxane-4,6-dione derivatives, which are precursors of chiral tetramic acid derivatives.

According to this process, an N-urethane-protected α-amino acid N-carboxy-anhydride is reacted with Meldrum's acid in an inert organic solvent medium in the presence of a tertiary amine.

This process makes it possible to conserve the chirality of the starting material and in particular to simplify the synthesis of 4-amino-3-hydroxy acids and the derivatives thereof via the tetramic acid route.

10 Claims, No Drawings

PROCESS FOR THE STEREOSPECIFIC PREPARATION OF 5-(1-HYDROXY-2-URETHANETHYLIDENE)-2,2-DIMETHYL-1,3-DIOXANE-4,6-DIONE DERIVATIVES, WHICH ARE PRECURSORS OF CHIRAL TETRAMIC ACID DERIVATIVES

The invention relates to a process for the stereospecific preparation of 5-(1-hydroxy-2-urethanethylidene)- 2,2-dimethyl-1,3-dioxane-4,6-dione derivatives, allowing chiral tetramic acid derivatives to be obtained. These tetramic acid derivatives are very useful for synthesizing 3-hydroxy-4-amino acids such as statine and the analogues thereof, which are very important amino acids in chemotherapy. The compounds of this family are in particular characteristic constituents of acid protease inhibitors and also of depsipeptides.

Several syntheses of statine and of the analogues thereof have been described. The most commonly used are based on the aldol condensation reaction of enolate esters and of α-acylamino-aldehydes (P. G. M. Wuts, Synthesis, 1989, 951).

These methods have a certain number of disadvantages, such as racemization or the production of diastereoisomers which it is subsequently necessary to separate, or alternatively reactants which are not very common are used.

Another route has been proposed which allows statine and the analogues thereof to be prepared using intermediates which are chiral tetramic acids (in particular P. Jouin et al., J. Chem. Soc. Perkin Trans, 1, 1987, 1177–1182). These are obtained by condensation of an N-protected chiral amino acid with Meldrum's acid in the presence of isopropenyl chloroformate and 4-N,N-dimethylaminopyridine, followed by a cyclization of the dioxane derivative obtained. Although this approach allows the stereospecificity to be conserved, it is, however, neither very economical nor very easy to implement. Isopropenyl chloroformate is an expensive and unstable reagent. The reaction conditions are very rigorous. The isopropenyl chloroformate must be added slowly to a solution of the other reactants maintained at a very low temperature, in the region of –5° C. Any change in the experimental procedure, for example in the order of introduction of the reactants, in the temperature or in the respective amounts of the reactants, leads to a lowering of the yields.

The aim of the present invention is to overcome these disadvantages and its subject is a process for the preparation of dioxane intermediates which is economical, simple, rapid and which allows the chirality of the asymmetric carbon of the starting amino acid derivative to be conserved.

According to the invention, 5-(1-hydroxy-2-urethanethylidene)- 2,2-dimethyl-1,3-dioxane-4,6-dione derivatives, precursors of N-protected chiral tetramic acids, are prepared by reacting N-urethane-protected α-amino acid N-carboxy-anhydrides (UNCA) with Meldrum's acid, in an inert organic solvent medium, in the presence of an amount greater than 2 equivalents relative to the N-carboxy-anhydride of at least one tertiary amine chosen from tertiary amines in which at least one radical is aliphatic or cycloaliphatic. The other radicals of the amines are very various, identical or different, such as for example aliphatic radicals, cycloaliphatic radicals, araliphatic radicals, aromatic hydrocarbon radicals or aromatic or non-aromatic heterocyclic radicals or radicals which are joined and form with the nitrogen atom a heterocycle possibly comprising other heteroatoms.

The reaction scheme is as follows:

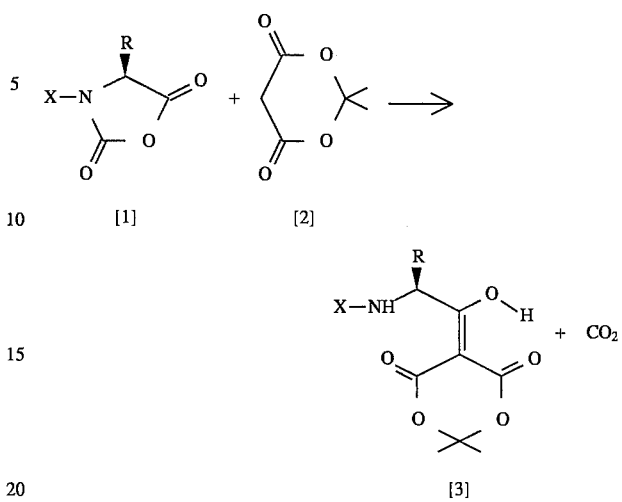

R representing an α-amino acid residue and X representing the protecting group forming the urethane function.

These dioxane-dione derivatives (3) may subsequently be converted in a known manner, for example as described in the articles by P. Jouin et al. mentioned above or by J. Poncet, J. Chem. Soc. Perkin Trans., 1, 1990, 611, first of all into N-protected tetramic acid derivatives (4) which are reduced to give 4-hydroxy-2-pyrrolidinone derivatives (5). On regioselective hydrolysis of the latter compounds, pure N-protected diastereoisomers of 3-hydroxy-4-amino acids (6), are obtained, such as statine or an analogue.

The reaction scheme for this conversion is as follows:

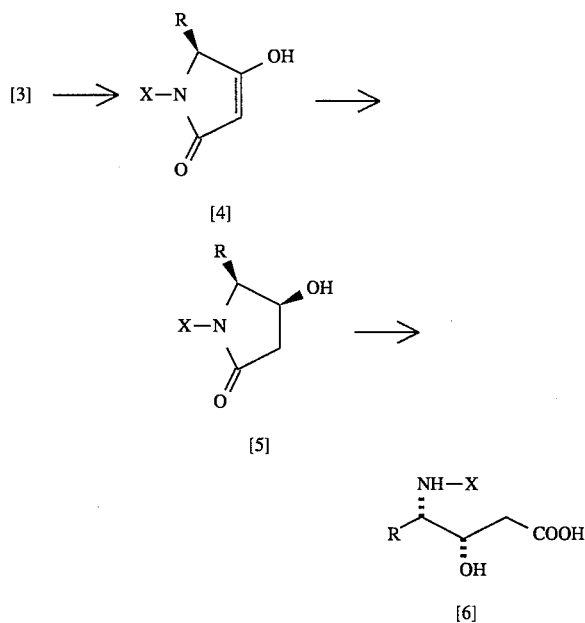

The N-urethane-protected α-amino acid N-carboxy-anhydrides (1) (UNCA) used as starting materials are known stable compounds which are found commercially or which may be prepared as described in the article in J. Am. Chem. Soc., vol 112, No. 20, 1990, 7414–7416.

When the side chains of the α-amino acids which form the anhydrides bear functional groups, the latter are generally protected by the usual protecting groups in peptide synthesis.

The amine function of the anhydride is protected by one of the protecting groups usually used for this function in peptide synthesis and which forms a urethane function. Preferred groups which may be mentioned are the (9-fluorenylmethyl)oxycarbonyl (Fmoc), tert-butyloxy-carbonyl (Boc), benzyloxycarbonyl (Z) and allyloxycarbonyl (Alloc) groups.

Meldrum's acid (isopropylidene malonate) is a known compound which is found commercially.

It was found that the N-urethane-protected α-amino acid N-carboxy-anhydrides could be made to react very readily with Meldrum's acid, in order to obtain the dioxane-dione derivatives which are precursors of tetramic acid derivatives, while at the same time conserving the chirality of the starting compound.

The presence of at least one tertiary amine is necessary for the reaction to take place.

Among the tertiary amines which are particularly useful, there may be mentioned those in which the aliphatic portion(s) each have from 1 to 8 carbon atoms and/or the cycloaliphatic portion(s) each have from 6 to 8 carbon atoms, these portions possibly being substituted with aromatic radicals, such as triethylamine, tributylamine, diisopropylethylamine, tricyclohexylamine, N,N-di(phenylethyl)methylamine, tertiary amines in which one radical consists of a cyclic aromatic system, such as N,N-dimethyl- or N,N-diethylaniline, 4,4'-bis(dimethylamino)benzophenone also known as Mischler's ketone, N,N-dimethylaminopyridine and those in which the nitrogen atom forms part of a heterocycle, such as N-methylmorpholine and N-methylimidazole.

Inexpensive tertiary amines are generally chosen. Diisopropylethylamine, triethylamine and N-methylmorpholine are very suitable.

The anhydride and Meldrum's acid are generally used in a stoichiometric amount and the tertiary amine is used in an amount greater than 2 equivalents relative to the anhydride, preferably in an amount in the region of 3 equivalents.

The reaction is carried out in an inert organic solvent medium. Suitable solvents which may be mentioned are aliphatic or aromatic hydrocarbons, which may or may not be chlorinated, such as dichloromethane, 1,2-dichloroethane, toluene, chlorobenzene, cyclic or acyclic ethers and ketones. Dichloromethane or tetrahydrofuran is often used.

Large amounts of solvents are generally not necessary. The process is often performed in a concentrated reaction medium.

It is preferable for the constituents to be anhydrous.

Contrary to other processes, it is not absolutely necessary to cool the reaction medium. Room temperature, in the region of 20° C., is very suitable for performing the process.

The desired dioxane-dione derivatives are generally obtained within a few minutes. They are very easily recovered in crude form using the usual treatments such as washing and evaporation of the solvents. They may subsequently be readily converted in a known manner into tetramic acid derivatives. If so desired, they may be purified by standard methods.

The process according to the invention makes it possible in particular to simplify the synthesis of 4-amino- 3-hydroxy acids and the derivatives thereof via the tetramic acids route, by means of the step of preparation of the dioxane-dione derivatives which is carried out from stable compounds, and which does not require the use of reactants which are expensive or difficult to handle, or specific reaction conditions, and which is rapid. The tetramic acids derived therefrom are obtained in good yields and are optically pure.

The examples which follow illustrate the invention without, however, limiting it.

In all the examples, the starting materials are in the (L) form. It is obvious that the process applies equally to the preparation of the compounds with the opposite configuration.

EXAMPLES 1 TO 16

The 5-(1-hydroxy-2-urethanethylidene)-2,2-dimethyl-1,3-dioxane-4,6-dione derivatives (3) are prepared according to the following general experimental procedure:

One equivalent of UNCA (1) and one equivalent of Meldrum's acid (2) are reacted in dichloromethane (DCM) or tetrahydrofuran (THF) (2 ml/mmol) at room temperature (in the region of 20° C.) in the presence of 3 equivalents of triethylamine, diisopropylethylamine or N-methylmorpholine. The reaction is monitored by thin layer chromatography (TLC) with the following eluent system: ethyl acetate (EtOAc)/methanol (MeOH)/acetic acid (AcOH): 95/3/2 (the ratios of the eluents are expressed by volume throughout the text). It is generally finished at the end of a few minutes. The reaction medium is taken up in DCM and washed with aqueous 5% $KHSO_4$ solution and then with water. It is subsequently dried over sodium sulphate and the organic phase is concentrated under reduced pressure in order to obtain the desired compound (3).

In order to verify that the dioxane-dione derivatives obtained conserve the configuration of the starting material, they are converted into tetramic acid derivatives (4), then these are converted to 4-hydroxy-2-pyrrolidinone derivatives (5) in the following way:

The crude derivative (3) obtained above is dissolved in methanol or ethyl acetate and the solution is brought to the reflux temperature. The reaction is monitored by TLC (EtOAc/MeOH/AcOH: 95/3/2 or EtOAc/hexane/AcOH: 7/3/1). It is finished in 1 to 2 hours. After evaporation, the reaction mixture is taken up in EtOAc and washed with aqueous 5% $KHSO_4$, saturated sodium bicarbonate and saturated NaCl solutions. After drying and evaporation, compound (4) is obtained.

In order to convert it into compound (5), it is taken up in a DCM/AcOH (10/1) mixture and cooled in an ice bath. 2 molar equivalents (8 hydride equivalents) of $NaBH_4$ are subsequently added portionwise over approximately 1 hour to the vigorously stirred reaction medium, which is maintained for a few hours at the same temperature. The reaction is monitored by TLC (EtOAc/MeOH/AcOH: 95/3/2 or DCM/EtOAc: 7/3). If necessary, more hydride is added. The reaction medium is subsequently hydrolysed by adding an ice-water mixture. After separation of the phases by settling, the organic phase is washed with water, dried and evaporated. The residual mixture is chromatographed on silica with the solvent system EtOAc/hexane: 5/5 or DCM/EtOAc: 7/3 and the pure 4-hydroxy-2-pyrrolidinone derivative (5) is obtained.

The results obtained from N-carboxy-anhydrides of various N-protected amino acids are collated in the following Tables I to III. The yields of isolated compounds are calculated in all the examples from the starting UNCA, with respect to the crude compounds obtained in Examples 1 to 13 and with respect to the purified compounds obtained in Examples 14 to 16.

In Examples 5 to 13, the tetramic acid derivatives (4) were prepared. The optical rotations were measured on the crude products. The mass spectra are in accordance with the expected structures. The ¹H NMR spectra (250 HMz) confirm the structure of the compounds.

In Examples 14 to 16, the 4-hydroxy-2-pyrrolidinone derivatives (5) were prepared and purified. The measurements carried out show that the chirality of the starting material was conserved.

According to the same general experimental procedure, the 4-hydroxy-2-pyrrolidinone derivatives (5) were also prepared from the UNCAs of Fmoc-L-Ala, Fmoc-L-Ile, Fmoc-L-Thr(OBut), Boc-L-Val, Boc-L-Ala, Z-L-Ala, Fmoc-L-Lys(Alloc) (Yield: 72%), Fmoc-L-Met (Yield: 80%).

Of the UNCA of Boc-L-Leucine, using the general experimental procedure described in the above examples. 1.62 g (Yield: 65%) of (4S,5S)-4-hydroxy-5-isobutyl- 1-t-butoxycarbonyl-2-pyrrolidinone are obtained, the characteristics of which are as follows: Melting point (mp)=92°–93° C.; Rf=0.58 (eluent: EtOAc/hexane 75/25), $[\alpha]_D^{20}$=+55°(c=1, MeOH); ¹H NMR (CDCl₃) δ ppm: 0.90(6H, dd, Me); 1.48(9H, s, Boc); 1.72(3H, m, CH and CH₂); 2.60(2H, dq, H-3); 4.15(1H, m, H-5); 4.50(1H, m, H-4).

1 g of this 4-hydroxy-2-pyrrolidinone is dissolved in 5 ml of acetone. 2 ml of 1M sodium hydroxide are added dropwise. After 2 hours, the reaction mixture is acidified care-

TABLE I

| Ex. | UNCA of the following amino acid: | Yield of compound (3) % | Rf (eluent A) | Rf (eluent B) | Melting point °C. |
|---|---|---|---|---|---|
| 1 | Fmoc-L-Lys(Boc) | 82 | 0.6 | 0.5 | 121–123 |
| 2 | Fmoc-L-Lys(Alloc) | 86 | 0.6 | 0.6 | 93–95 |
| 3 | Fmoc-L-Thr(OBu) | 85 | 0.655 | 0.75 | 98–102 |
| 4 | Alloc-L-Val | 50 | 0.43 | 0.58 | 105–110 |

Eluent A: CHCl₃/MeOH/AcOH: 180/10/5;
Eluent B: EtOAC/MeOH/AcOH: 95/3/2.

TABLE II

| Ex. | UNCA of the following amino acid: | Yield of compound (4) % | Rf (eluent A) | Rf (eluent B) | $[\alpha]_D^{20}$ (C = 1,MeOH) | Mass spectrum, FAB+ |
|---|---|---|---|---|---|---|
| 5 | Fmoc-L-Phe | 84 | 0.45 | 0.57 | +104° | 412 |
| 6 | Boc-L-Phe | 80 | 0.37 | 0.49 | +205° | 290 |
| 7 | Z-L-Phe | 82 | 0.35 | 0.55 | +150° | 324 |
| 8 | Fmoc-L-Leu | 79 | 0.54 | | +66° | |
| 9 | Z-L-Leu | 76 | 0.51 | | +44° | |
| 10 | Fmoc-L-Val | 63 | 0.61 | 0.68 | +44° | 364 |
| 11 | Z-L-Val | 80 | 0.75 | 0.57 | +54° | 276 |
| 12 | Boc-L-Trp(For) | 60 | 0.37 | 0.35 | +113° | 357 |
| 13 | Fmoc-L-Lys(Boc) | 75 | 0.52 | 0.80 | +46° | 493 |

Eluent A: CHCl₃/MeOH/AcOH: 180/10/5;
Eluent B: EtOAc/hexane/AcOH: 7/3/1.
For = formyl.

TABLE III

| Ex. | UNCA of the following amino acid: | Yield of compound (5) % | Rf (eluent A) | Rf (eluent B) | $[\alpha]_D^{20}$ (C = 1,MeOH) | Mass spectrum, FAB+ |
|---|---|---|---|---|---|---|
| 14 | Boc-L-Leu | 65 | 0.50 | | +55° | 258 |
| 15 | Fmoc-L-Leu | 60 | | 0.65 | +42° | 379 |
| 16 | Z-L-Leu | 60 | | 0.46 | +58° | 292 |

Eluent A: CHCl₃/MeOH/AcOH: 180/10/5;
Eluent B: DCM/EtOAc: 7/3.

EXAMPLE 17

Preparation of (3S,4S)-6-methyl-4-t-butoxycarbonylamino-3-hydroxyheptanoic acid (Boc-statine)

In order to ensure that the process of the invention allows statine and the analogues thereof to be obtained with the desired configuration, Boc-statine is prepared from 2.49 g fully with dilute hydrochloric acid to pH 3–4. The Boc-statine obtained is precipitated by adding water, drained, washed with water and then with hexane and dried under vacuum in the presence of potassium hydroxide pellets. 810 mg of this statine are thus obtained, in the form of a white solid having the following characteristics: mp=120°–120° C.; Rf=0.52 (eluent CHCl₃/MeOH/AcOH: 180/10/5); $[\alpha]_D^{20}$=+41.9°(c=1,MEOH); ¹HNMR(DMSO-d₆) δ ppm: 0.85(6H,dd,CH₃); 1.26(2H,m,CH₂); 1.37(9H,s,Boc);

1.55(1H,m,CH); 2.21(2H,m,H-2); 3.51(1H,m,H-4); 3.80(1H,m,H-3); 6.31(1H,d,NH); MS-FAB+: 276.

We claim:

1. Process for the preparation of 5-(1-hydroxy-2-urethanethylidene)- 2,2-dimethyl-1,3-dioxane-4,6-dione derivatives, wherein an N-urethane-protected α-amino acid N-carboxy-anhydride is reacted with Meldrum's acid, in an inert organic solvent medium, in the presence of an amount greater than 2 equivalents relative to the N-carboxy-anhydride of at least one tertiary amine chosen from tertiary amines in which at least one radical is aliphatic or cycloaliphatic.

2. Process according to claim 1, wherein the aliphatic portion(s) of the amine each have from 1 to 8 carbon atoms and the cycloaliphatic portion(s) each have from 6 to 8 carbon atoms.

3. Process according to claim 1, wherein the tertiary amine is chosen from diisopropylethylamine, triethylamine and N-methylmorpholine.

4. Process according to claim 1, wherein the tertiary amine is added in an amount in the region of 3 equivalents relative to the N-carboxy-anhydride.

5. Process according to claim 1, wherein the anhydride and the Meldrum's acid are made to react in a stoichiometric amount.

6. Process according to claim 1, wherein the protecting group of the amine function of the anhydride is chosen from (9-fluorenylmethyl)oxycarbonyl, tert-butyloxycarbonyl and benzyloxycarbonyl groups.

7. Process according to claim 1, wherein the protecting group of the amine function of the anhydride is the allyloxycarbonyl group.

8. Process according to claim 1, wherein the functional groups borne by the side chains of the α-amino acid forming the N-carboxy-anhydride are protected.

9. Process according to claim 1, wherein the solvent medium is chosen from aliphatic or aromatic, chlorinated or unchlorinated hydrocarbons, cyclic or acyclic ethers and ketones.

10. Process according to claim 1, wherein the 5-(1-hydroxy- 2-urethanethylidene)-2,2-dimethyl-1,3-dioxane-4,6-dione derivatives are recovered in crude form.

* * * * *